United States Patent
Kim et al.

(10) Patent No.: US 11,852,619 B2
(45) Date of Patent: Dec. 26, 2023

(54) APPARATUS FOR INSPECTING MEAT, SYSTEM FOR INSPECTING MEAT INCLUDING THE SAME, REFRIGERATOR INCLUDING THE SAME, AND METHOD OF INSPECTING MEAT

(71) Applicants: SAMSUNG ELECTRONICS CO., LTD., Suwon-si (KR); CHUNG ANG University Industry Academic Cooperation Foundation, Seoul (KR)

(72) Inventors: Unjeong Kim, Osan-si (KR); Hyungbin Son, Seoul (KR); Suyeon Lee, Seoul (KR)

(73) Assignees: SAMSUNG ELECTRONICS CO., LTD., Suwon-si (KR); CHUNG ANG University Industry Academic Cooperation Foundation, Seoul (KR)

(*) Notice: Subject to any disclaimer, the term of this patent is extended or adjusted under 35 U.S.C. 154(b) by 172 days.

(21) Appl. No.: 17/479,377

(22) Filed: Sep. 20, 2021

(65) Prior Publication Data

US 2022/0091087 A1 Mar. 24, 2022

(30) Foreign Application Priority Data

Sep. 21, 2020 (KR) .................. 10-2020-0121798
Jul. 26, 2021 (KR) .................. 10-2021-0097962

(51) Int. Cl.
*G01N 33/12* (2006.01)
*F25D 29/00* (2006.01)
(Continued)

(52) U.S. Cl.
CPC ............ *G01N 33/12* (2013.01); *F25D 29/00* (2013.01); *G01N 21/6456* (2013.01);
(Continued)

(58) Field of Classification Search
CPC ............ F25D 29/00; G01N 21/6456; G01N 21/6486; G06T 7/0002; G06T 2207/10064;
(Continued)

(56) References Cited

U.S. PATENT DOCUMENTS 5,621,215 A 4/1997 Waldroup et al.
8,625,856 B2 1/2014 Chao et al.
(Continued)

FOREIGN PATENT DOCUMENTS

CN 107509908 A 12/2017
CN 108662843 A 10/2018
(Continued)

OTHER PUBLICATIONS

Ait-Kaddour, A., et al., "Potential of fluorescence spectroscopy to predict fatty acid composition", Meat Science, vol. 113, 2016, pp. 124-131.
(Continued)

*Primary Examiner* — Michael A Lyons
*Assistant Examiner* — Omar H Nixon
(74) *Attorney, Agent, or Firm* — Sughrue Mion, PLLC

(57) ABSTRACT

Provided is a meat inspection apparatus including a light source configured to emit a plurality of inspection lights to a plurality of regions of meat, respectively, a light detector configured to generate a plurality of emission spectrum signals based on measuring a plurality of fluorescences emitted from the plurality of regions, and a processor configured to receive the plurality of emission spectrum signals from the light detector, generate hyperspectral images of the meat based on the plurality of emission spectrum signals, and obtain a state of the meat based on the hyperspectral images, wherein the processor is further configured to obtain the state of the meat for a plurality of sub-regions in each of the plurality of regions.

30 Claims, 17 Drawing Sheets

(51) Int. Cl.
*G01N 21/64* (2006.01)
*G06T 7/00* (2017.01)

(52) U.S. Cl.
CPC ....... *G01N 21/6486* (2013.01); *G06T 7/0002* (2013.01); *G06T 2207/10064* (2013.01); *G06T 2207/10152* (2013.01); *G06T 2207/20021* (2013.01); *G06T 2207/20221* (2013.01)

(58) Field of Classification Search
CPC . G06T 2207/10152; G06T 2207/20021; G06T 2207/20221
USPC ........................................................ 356/317
See application file for complete search history.

(56) References Cited

U.S. PATENT DOCUMENTS

| | | | |
|---|---|---|---|
| 9,322,769 B2 | 4/2016 | Alfano et al. | |
| 2008/0199080 A1* | 8/2008 | Subbiah | G01N 21/31 |
| | | | 382/190 |
| 2011/0128373 A1* | 6/2011 | Goldberg | G06V 10/764 |
| | | | 382/110 |
| 2013/0010294 A1 | 1/2013 | Matsuda et al. | |
| 2014/0300891 A1 | 10/2014 | Alfano et al. | |
| 2017/0319073 A1* | 11/2017 | DiMaio | A61B 5/0075 |
| 2019/0008173 A1 | 1/2019 | Park et al. | |
| 2019/0339203 A1* | 11/2019 | Miller | G01J 3/2823 |

FOREIGN PATENT DOCUMENTS

| | | |
|---|---|---|
| CN | 110966833 A | 4/2020 |
| CN | 211426274 U | 9/2020 |
| JP | 2002162358 A | 6/2002 |
| JP | 2012122680 A | 6/2012 |
| JP | 201319673 A | 1/2013 |
| JP | 2014153163 A | 8/2014 |
| KR | 1020170079525 A | 7/2017 |

OTHER PUBLICATIONS

Pu, Y., et al., "Spoilage of foods monitored by native fluorescence spectroscopy with selective excitation wavelength", Proceedings of SPIE, vol. 9314, 2015, pp. 1-11.
Marchi, M., "On-line prediction of beef quality traits using near infrared spectroscopy", Meat Science, vol. 94, 2013, pp. 455-460.
Communication dated Feb. 21, 2022 by the European Patent Office in counterpart European Patent Application No. 21197434.0.
Wang, Meng, "Fluorescence Image Based Food Quality Measurement", Feb. 1, 2014, The University of Tokyo, XP055889551. (56 pages total).

* cited by examiner

APPARATUS FOR INSPECTING MEAT, SYSTEM FOR INSPECTING MEAT INCLUDING THE SAME, REFRIGERATOR INCLUDING THE SAME, AND METHOD OF INSPECTING MEAT

CROSS-REFERENCE TO RELATED APPLICATION

This application claims priority to Korean Patent Application No. 10-2020-0121798, filed on Sep. 21, 2020 in the Korean Intellectual Property Office, and Korean Patent Application No. 10-2021-0097962, filed on Jul. 26, 2021 in the Korean Intellectual Property Office, the disclosure of which is incorporated by reference herein in its entirety.

BACKGROUND

1. Field

Example embodiments of the present disclosure relate to a meat inspection apparatus, a meat inspection system, a refrigerator, and a meat inspection method.

2. Description of Related Art

Maintaining freshness of meat after animals are slaughtered and until meat thereof is supplied to consumers is one of the important issues in a meat distribution process. Furthermore, freshness of meat is one of the important factors for determining the quality of meat.

Several indicators may be used to evaluate the quality and characteristics of meat. For example, appearance evaluation is used for checking browning and appearance deformation by using a digital camera, chromaticity is measured by using a color difference meter, PH is measured, thiobarbituric acid (TBA) is used for measuring the concentration of malonaldehyde, which is a secondary product of oxidation of fat generated as fat and oil that are acidified, a volatile basic nitrogen (VBN) method of measuring an increase in VBN such as ammonia, trimethylamine (TMA), dimethylamine (DMA), and the like in muscles of fish is employed, and sensory evaluation is used according to a test method presented in a food code.

A meat quality characteristic evaluation method of the related art includes an expert-level indexing method used in slaughterhouses or by large retailers and it is not used by general consumers. Furthermore, the meat quality characteristic evaluation method of the related art is either a destruction method or a method in which a subjective opinion may occur. Therefore, indicators that may be more easily used in a state of meat used for a general consumer are required.

SUMMARY

One or more example embodiments provide a meat inspection apparatus for determining the state of meat.

One or more example embodiments also provide a meat inspection system including a meat inspection apparatus for determining the state of meat.

One or more example embodiments also provide a refrigerator including a meat inspection apparatus for determining the state of meat.

Additional aspects will be set forth in part in the description which follows and, in part, will be apparent from the description, or may be learned by practice of the example embodiments of the disclosure.

According to an aspect of an example embodiment, there is provided a meat inspection apparatus including a light source configured to emit a plurality of inspection lights to a plurality of regions of meat, respectively, a light detector configured to generate a plurality of emission spectrum signals based on measuring a plurality of fluorescences emitted from the plurality of regions, and a processor configured to receive the plurality of emission spectrum signals from the light detector, generate hyperspectral images of the meat based on the plurality of emission spectrum signals, and obtain a state of the meat based on the hyperspectral images, wherein the processor is further configured to obtain the state of the meat for a plurality of sub-regions in each of the plurality of regions.

The light source may be further configured to emit the plurality of inspection lights such that adjacent regions of the plurality of regions partially overlap each other.

The processor may be further configured to generate a plurality of hyperspectral sub-images of the plurality of region, merge the plurality of hyperspectral sub-images to generate the hyperspectral images, and remove a hyperspectral image corresponding to a region in which the adjacent regions overlap with each other from one of hyperspectral sub-images of the adjacent regions based on the plurality of hyperspectral sub-images being merged.

The light source may be further configured to emit the plurality of inspection lights to the plurality of regions at different times.

The light source may be disposed at a plurality of positions facing the plurality of regions, and the light source may be further configured to emit the plurality of inspection lights to the plurality of regions facing the plurality of positions, respectively.

The light source may include a plurality of sub-light sources configured to emit the plurality of inspection lights to the plurality of regions, respectively, and the light detector may include a plurality of sub-light detectors configured to measure the plurality of fluorescences emitted from the plurality of regions, and the processor may be further configured to receive the plurality of emission spectrum signals from the plurality of sub-light detectors.

The state of the meat may include freshness, and the processor may be further configured to obtain a content of porphyrin in the meat based on the hyperspectral images and obtain the freshness of the meat based on the content of porphyrin.

The state of the meat may include freshness, and the processor may be further configured to obtain at least one of a content of collagen in the meat, a content of NADH in the meat, and a content of flavin in the meat based on the hyperspectral images, and obtain the freshness of the meat based on at least one of the content of collagen, the content of NADH, and the content of flavin or based on a ratio therebetween.

The state of the meat may include a degree of fat, and the processor may be further configured to obtain a content of fatty acid in the meat based on the hyperspectral images and obtain the degree of fat of the meat based on the content of fatty acid.

The meat may include a plurality of individual meats, and the processor may be further configured to distinguish the plurality of individual meats based on hyperspectral images of the plurality of individual meats and obtain a state of each of the plurality of individual meats.

The light source may include a first light source array including a plurality of light sources disposed in a first direction.

The light source may further include a transmission window, and the plurality of fluorescences emitted from the plurality of regions may pass through the transmission window to reach the light detector.

The light source may further include a second light source array spaced apart from the first light source array in a second direction with the transmission window interposed therebetween, wherein the second direction crosses the first direction, and wherein the second light source array includes a plurality of light sources disposed in the first direction.

Central wavelengths of the plurality of inspection lights may range from among 335 nm to 370 nm.

According to another aspect of an example embodiment, there is provided a meat inspection system including a meat inspection apparatus including a light source configured to emit a plurality of inspection lights to a plurality of regions of meat, respectively, a light detector configured to generate a plurality of emission spectrum signals based on measuring a plurality of fluorescences emitted from the plurality of regions, and a processor configured to receive the plurality of emission spectrum signals from the light detector, generate hyperspectral images of the meat based on the plurality of emission spectrum signals, and obtain a state of the meat based on the hyperspectral images, wherein the processor is further configured to obtain the state of the meat for a plurality of sub-regions in each of the plurality of regions, and a display device configured to receive state information of the meat from the meat inspection apparatus and output the state information of the meat.

The display device may be connected to the meat inspection apparatus by wire or wirelessly.

According to another aspect of an example embodiment, there is provided a refrigerator including a main body having a plurality of storage spaces, doors configured to open and close the plurality of storage spaces, and a meat inspection apparatus provided in at least one of the plurality of storage spaces, wherein the meat inspection apparatus includes a light source configured to emit a plurality of inspection lights to a plurality of regions of meat, respectively, a light detector configured to generate a plurality of emission spectrum signals based on measuring a plurality of fluorescences emitted from the plurality of regions, and a processor configured to receive the plurality of emission spectrum signals from the light detector, generate hyperspectral images of the meat based on the plurality of emission spectrum signals, and obtain a state of the meat based on the hyperspectral images, wherein the processor is further configured to obtain the state of the meat for a plurality of sub-regions in each of the plurality of regions.

The refrigerator may further include a display device disposed on one of the doors, wherein the display device is configured to receive state information of meat from the meat inspection apparatus and output the state information of the meat.

The refrigerator may further include a communication interface configured to communicate with an external apparatus, wherein the communication interface is further configured to transmit the state information of the meat to the external apparatus.

According to another aspect of an example embodiment, there is provided a meat inspection method including emitting a plurality of inspection lights to a plurality of regions of meat, detecting a plurality of fluorescences emitted from the plurality of regions to generate a plurality of emission spectrum signals, generating hyperspectral images of the meat based on the plurality of emission spectrum signals, and obtaining a state of the meat based on the hyperspectral images, wherein the obtaining of the state of the meat is performed for a plurality of sub-regions of each of the plurality of regions.

The emitting of the plurality of inspection lights may further include emitting the plurality of inspection lights so that adjacent regions of the plurality of regions partially overlap each other.

The generating of the hyperspectral images may further include generating a plurality of hyperspectral sub-images of the plurality of regions, removing a hyperspectral image of a region in which the adjacent regions overlap each other from one of hyperspectral sub-images of the adjacent regions, and merging the plurality of hyperspectral sub-images.

The emitting of the plurality of inspection lights to the plurality of regions of the meat may be performed at different times.

The emitting of the plurality of inspection lights to the plurality of regions of the meat may be performed simultaneously.

The obtaining of the state of the meat may further include obtaining a content of porphyrin in the meat based on the hyperspectral images and obtaining freshness of the meat based on the content of porphyrin.

The obtaining of the state may further include obtaining at least one of a content of collagen in the meat, a content of NADH in the meat, and a content of flavin in the meat based on the hyperspectral images, and obtaining freshness of the meat based on at least one of the content of collagen, the content of NADH, and the content of flavin or based on a ratio therebetween.

The obtaining of the state may further include obtaining a content of fatty acid in the meat based on the hyperspectral images and obtaining a degree of fat of the meat based on the content of the fatty acid.

Central wavelengths of the plurality of inspection lights may range from among 340 nm to 370 nm.

The meat may include a plurality of individual meats, and the obtaining of the state of the meat may further include distinguishing the plurality of individual meats based on hyperspectral images of the plurality of individual meats and obtaining a state of each of the plurality of individual meats.

According to another aspect of an example embodiment, there is provided a meat inspection apparatus including a light source configured to emit a plurality of inspection lights to a plurality of regions of meat, respectively, the light source including a first light source array, a second light source array that is spaced apart from the first light source array, and a transmission window disposed between the first light source array and the second light source array, a light detector configured to generate a plurality of emission spectrum signals based on measuring a plurality of fluorescences emitted from the plurality of regions, and a processor configured to receive the plurality of emission spectrum signals from the light detector, generate hyperspectral images of the meat based on the plurality of emission spectrum signals, and obtain a state of the meat based on the hyperspectral images.

BRIEF DESCRIPTION OF THE DRAWINGS

The above and/or other aspects, features, and advantages of example embodiments will be more apparent from the following description taken in conjunction with the accompanying drawings, in which.

DETAILED DESCRIPTION

Figure 1:
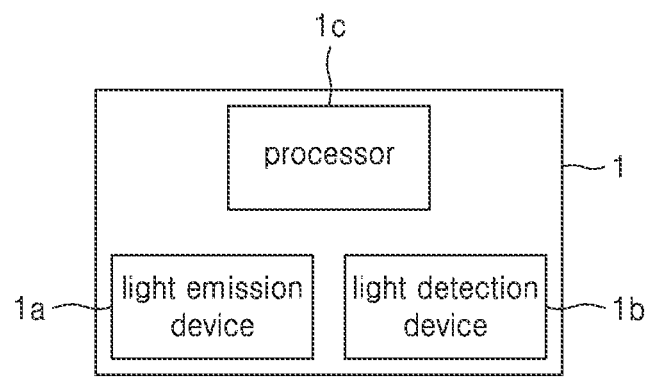
FIG. 1 is a block diagram of a meat inspection apparatus according to an example embodiment.

Reference will now be made in detail to example embodiments of which are illustrated in the accompanying drawings, wherein like reference numerals refer to like elements throughout. In this regard, the example embodiments may have different forms and should not be construed as being limited to the descriptions set forth herein. Accordingly, the example embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

Hereinafter, example embodiments will be described in detail with reference to the accompanying drawings. The example embodiments to be described are merely examples, and various modifications may be made from the example embodiments. In the following drawings, the same reference numerals refer to the same configuration elements, and a size of each configuration element in the drawings may be exaggerated for the sake of clear and convenient description.

Hereinafter, what is described as "upper" or "above" may include not only those directly above in contact therewith, but also those above without being in contact therewith.

Singular expressions include plural expressions unless the context clearly indicates otherwise. In addition, when a portion "includes" a certain configuration element, this indicates that other configuration elements may be further included rather than excluding other configuration elements unless specifically stated to the contrary.

FIG. 1 is a block diagram of a meat inspection apparatus according to an example embodiment.

Referring to FIG. 1, a meat inspection apparatus 1 including a light emission device 1a, a light detection device 1b, and a processor 1c may be provided. The light emission device 1a may emit inspection light. The light emission device 1a may emit inspection light to meat. For example, the light emission device 1a may emit inspection light having a wavelength of approximately 335 nm to approximately 370 nm. For example, the light emission device 1a may include a light emitting diode (LED).

The light detection device 1b may detect light incident on the light detection device 1b. For example, the light detection device 1b may detect fluorescence emitted from meat. The fluorescence may indicate that various indicator materials of meat absorb and emit light provided from the light emission device 1a. For example, the indicator material may include at least one of porphyrin, collagen, NADH, flavin, and fatty acid. The light detection device 1b may detect fluorescence by spectroscopy. Thus, the light detection device 1b may generate an emission spectrum signal. The emission spectrum signal may be a spectrum signal of fluorescence detected by the light detection device 1b.

The processor 1c may receive the emission spectrum signal from the light detection device 1b. The processor 1c may acquire a hyperspectral image of meat based on the received emission spectrum signal. The hyperspectral image of meat may be a combination of spectral distribution of each position of meat. The processor 1c may measure a distribution of the content of index substance in the meat by using the hyperspectral image. The processor 1c may determine a state of the meat based on the distribution of the content of the index substance in the meat.

According to an example embodiment, the meat inspection apparatus 1 may determine and obtain a state of meat based on hyperspectral image of meat.

Figure 2:
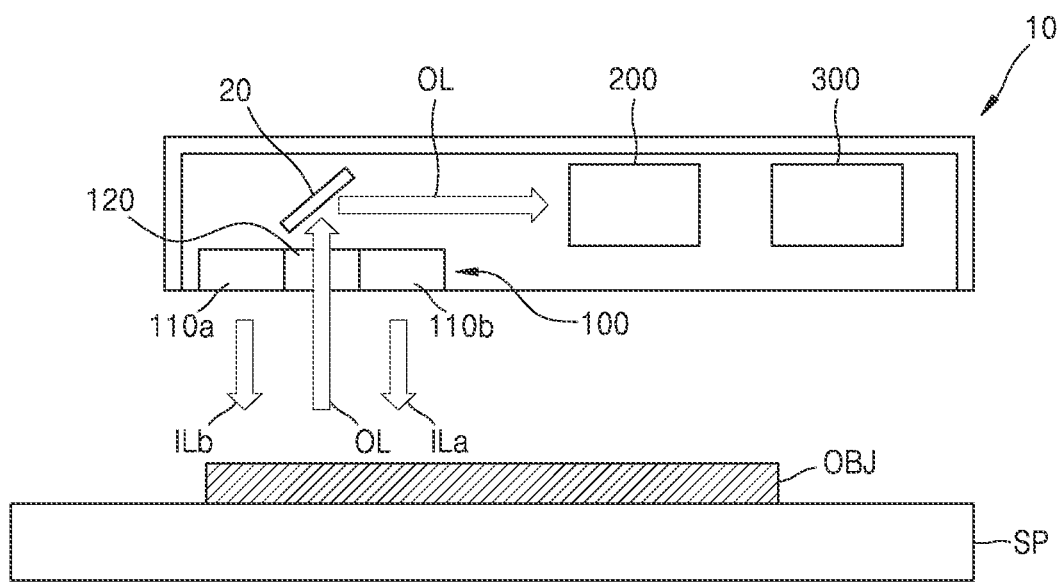
FIG. 2 is a conceptual view of a meat inspection apparatus according to an example embodiment.
Figure 3:
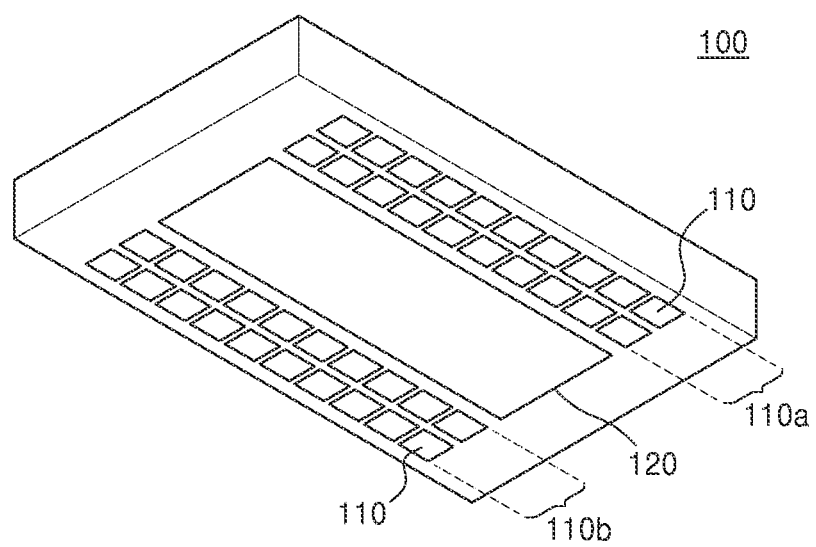
FIG. 3 is an example conceptual view of a light source of FIG. 2.
Figure 4:
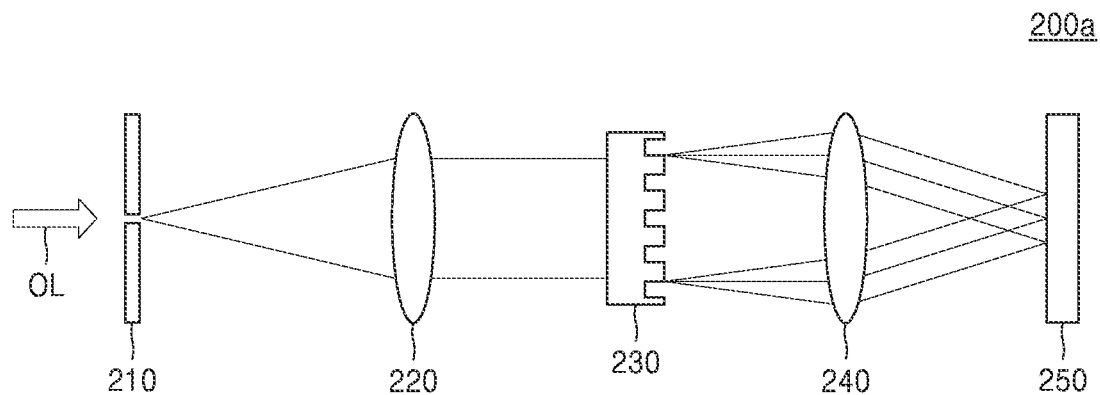
FIG. 4 is a conceptual view illustrating an example of a light detector of FIG. 2.
Figure 5:
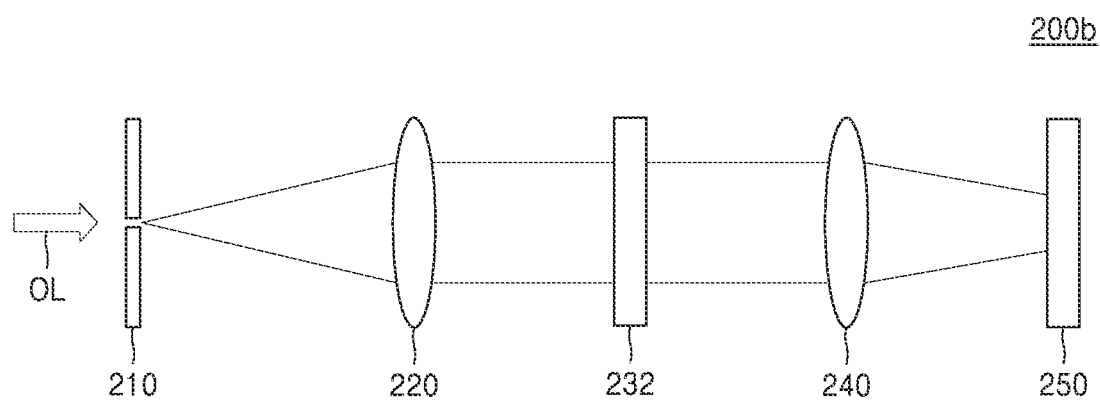
FIG. 5 is a conceptual view illustrating an example of the light detector of FIG. 2.

FIG. 2 is a conceptual view of a meat inspection apparatus according to an example embodiment. FIG. 3 is an example conceptual view of the light source of FIG. 2. FIG. 4 is a conceptual view illustrating an example of the light detector of FIG. 2. FIG. 5 is a conceptual view illustrating an example of the light detector of FIG. 2.

Referring to FIGS. 2 to 5, a meat inspection apparatus 10 may include a light source 100, a light detector 200, and a processor 300. Meat OBJ may be placed on a support SP. The meat OBJ may include meat of mammalian animal such as cattle, pig, sheep, and horse, meat of bird such as chicken, duck, and pheasant, or meat of fish such as tuna, mackerel, and salmon. However, the meat OBJ is not limited to the above examples.

The light source 100 may face the meat OBJ. The light source 100 may emit inspection light ILa and ILb onto the meat OBJ. As illustrated in FIG. 3, the light source 100 may include a first light source array 110a, a second light source array 110b, and a transmission window 120. The first light source array 110a and the second light source array 110b may be spaced apart from each other with the transmission window 120 therebetween. Each of the first light source array 110a and the second light source array 110b may include a plurality of light sources 110 arranged in one direction. For example, the plurality of light sources 110 may be arranged along the transmission window 120. Although FIG. 3 illustrates that the plurality of light sources 110 of the first light source array 110a and the second light source array 110b respectively form two rows, embodiments are not limited thereto. The plurality of light sources 110 may include, for example, light emitting diodes (LEDs).

The meat OBJ exposed to the inspection light ILa and ILb may emit fluorescence OL. The fluorescence OL may pass through the transmission window 120 provided in the light source 100 of the meat inspection apparatus 10. The transmission window 120 may include a transparent material. For example, the transmission window 120 may be transparent plastic or glass, and the transmission window 120 may include a material having high durability against a low temperature. The fluorescence OL may be provided to the light detector 200. For example, an optical path of the fluorescence OL may be adjusted by an optical path control element 20 so that the fluorescence OL is provided to the light detector 200. The light detector 200 may include a hyperspectral camera.

According to an example embodiment, the light detector 200a may include a dispersion element 230 as illustrated in FIG. 4. The light detector 200a (200) may include a slit element 210, a collimating lens 220, a dispersion element 230, a condensing lens 240, and an image sensor 250. The slit element 210 may be used to extract a desirable portion of the fluorescence OL. For example, the fluorescence OL passing through the slit element 210 may be transmitted to the collimating lens 220. The collimating lens 220 may adjust a size of the fluorescence OL so that the fluorescence OL becomes parallel light or convergent light. For example, the collimating lens 220 may include a convex lens. The dispersion element 230 may disperse the fluorescence OL provided from the collimating lens 220. Although the dispersion element 230 is illustrated as a grid, embodiments are not limited thereto. In another example embodiment, the dispersion element 230 may be a prism. The spectroscopic fluorescence OL may pass through the condensing lens 240 to be provided to the image sensor 250. For example, the condensing lens 240 may include a convex lens. The spectroscopic fluorescence OL may be provided to different positions of the image sensor 250 according to a wavelength. The image sensor 250 may measure the spectroscopic fluorescence OL provided from the dispersion element 230. The image sensor 250 may generate a spectrum signal of the fluorescence OL. The spectrum signal of the fluorescence OL may be an emission spectrum signal. The image sensor 250 may provide the emission spectrum signal to the processor 300.

According to an example embodiment, as illustrated in FIG. 5, a light detector 200b (200) may include a spectroscopic filter 232. The light detector 200b may include the slit element 210, the collimating lens 220, a spectral filter 232, the condensing lens 240, and the image sensor 250. The slit element 210, the collimating lens 220, the condensing lens 240, and the image sensor 250 may be substantially the same as described with reference to FIG. 4. The spectral filter 232 may be a set of filters that pass each light of a different wavelength band. The spectral filter 232 may filter the fluorescence OL provided from the collimating lens 220 so that the fluorescence OL has spatially different wavelengths. For example, portions of fluorescence passing through different regions of the spectral filter 232 may have different wavelengths. The fluorescence OL filtered by the spectral filter 232 may pass through the condensing lens to be provided to the image sensor 250. The image sensor 250 may generate an emission spectrum signal for the fluorescence OL. The image sensor 250 may provide the emission spectrum signal to the processor 300.

The processor 300 may generate a hyperspectral image of the meat OBJ based on the emission spectrum signal. The hyperspectral image of the meat OBJ may be generated by merging spectral distribution information on each position of the meat OBJ. The hyperspectral image of the meat OBJ may be a set of spectral distributions of each position of the meat OBJ.

The processor 300 may determine a state of each position of the meat OBJ based on the hyperspectral image of the meat OBJ. For example, the state of the meat OBJ may be freshness of the meat OBJ or fatness of meat OBJ.

For example, the freshness of meat may be determined based on at least one of content of porphyrin, content of collagen, content of NADH, and content of flavin, or based on a content ratio thereof. The processor 300 may measure the content of porphyrin based on a spectral distribution of a wavelength band of approximately 570 nm to approximately 630 nm. The processor 300 may measure the content of collagen based on a spectral distribution of a wavelength band of approximately 360 nm to approximately 420 nm. The processor 300 may measure the content of NADH based on a spectral distribution of a wavelength band of approximately 430 nm to approximately 550 nm. The processor 300 may measure the content of flavin based on a spectral distribution of a wavelength band of approximately 500 nm to approximately 550 nm.

For example, the fatness of meat may be measured by content of fatty acid in the meat. The processor 300 may measure content of the fatty acid based on a spectral distribution of a wavelength band of approximately 430 nm to approximately 500 nm.

According to an example embodiment, the meat inspection apparatus 10 may be configured to determine and obtain a state of the meat OBJ by using a hyperspectral image of the meat OBJ.

Figure 6:
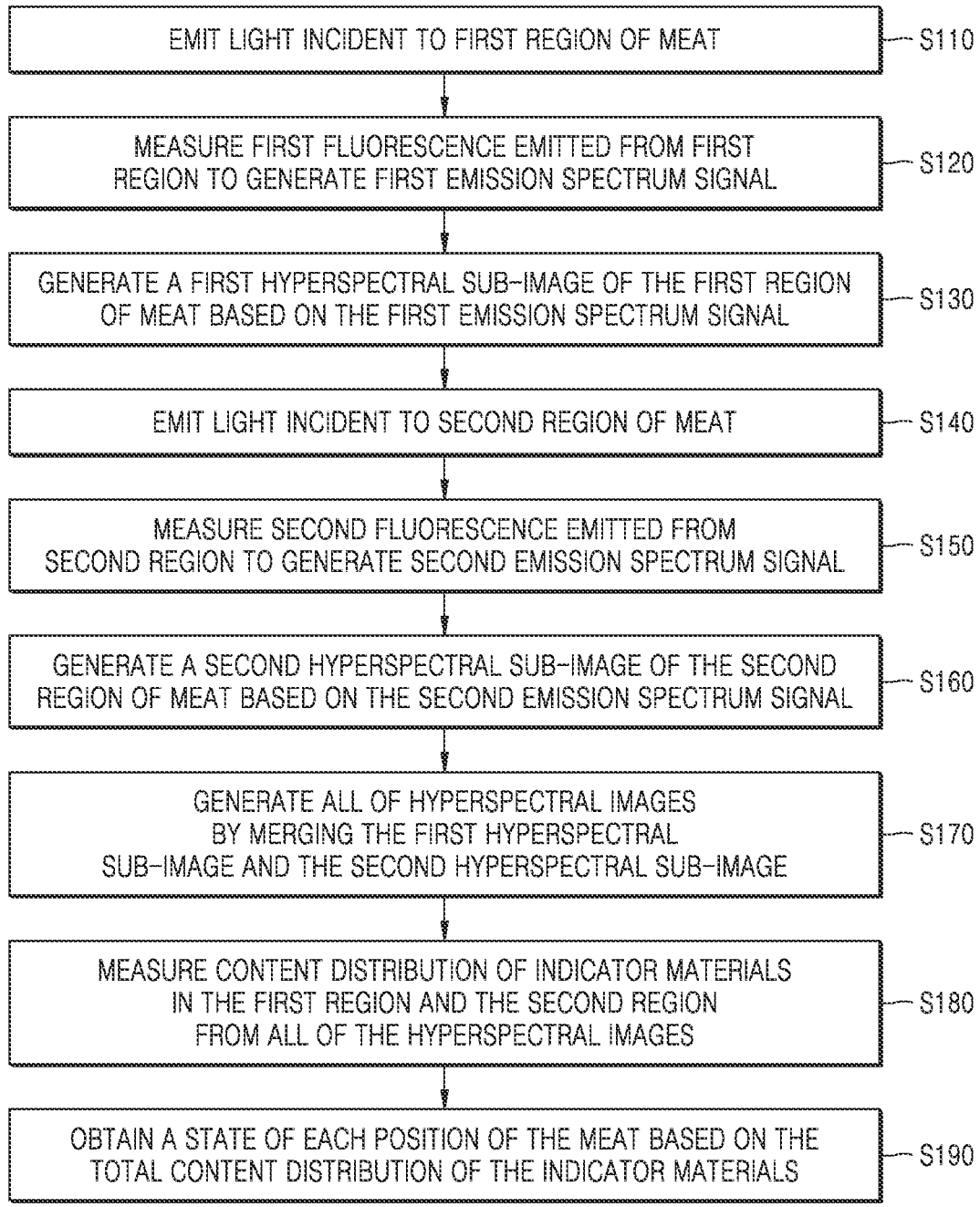
FIG. 6 is a flowchart illustrating a meat inspection method according to an example embodiment.

FIG. 6 is a flowchart illustrating a meat inspection method according to an example embodiment. FIGS. 7 to 10 are conceptual views illustrating the meat inspection method of FIG. 6. The content described with reference to FIGS. 2 to 5 may not be repeated.

Figure 7:
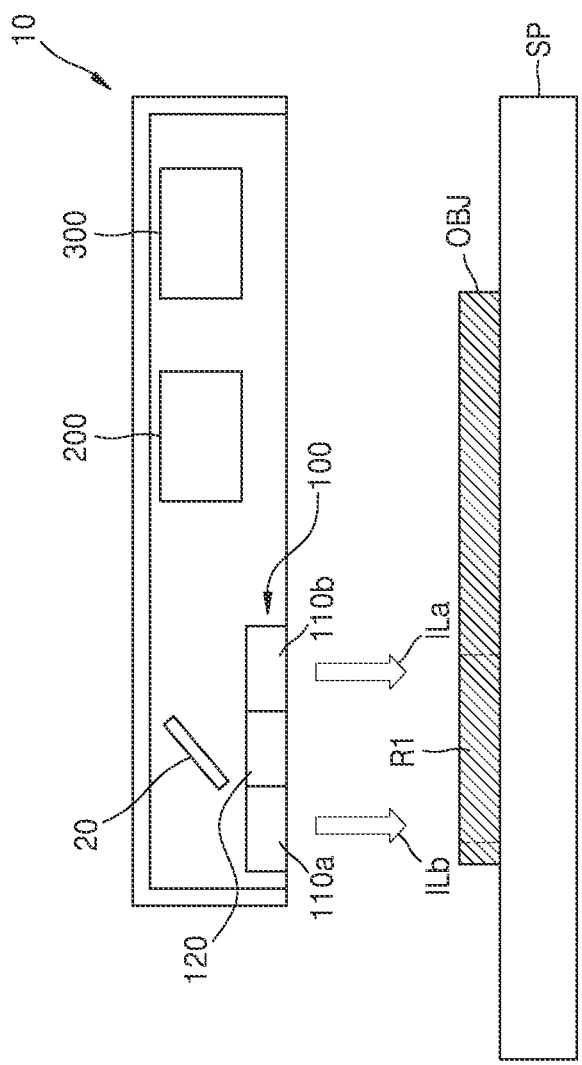
FIGS. 7, 8, 9, and 10 are conceptual views illustrating the meat inspection method of FIG. 6.

Referring to FIGS. 6 and 7, first inspection light ILa and ILb may be emitted to a first region R1 of the meat OBJ (S110). The first inspection light ILa and ILb may be emitted from the light source 100. A central wavelength of the first inspection light ILa and ILb may be selected from among approximately 335 nm to approximately 370 nm. The light source 100 may be arrange at a position facing the first region R1 and may emit the first inspection light ILa and ILb.

Figure 8:
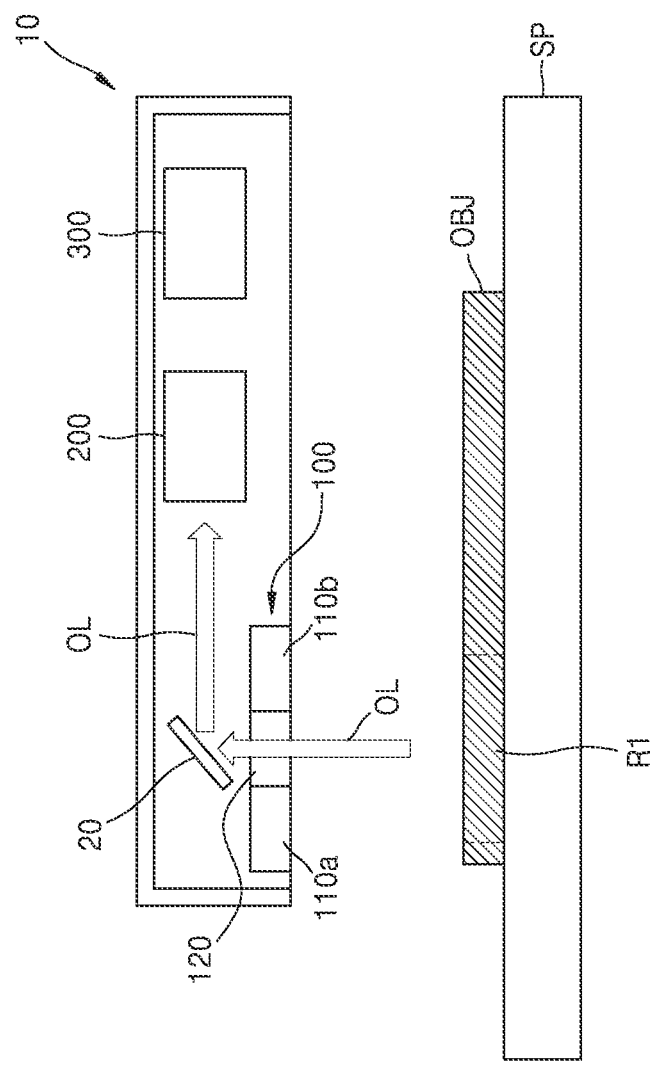

Referring to FIGS. 6 and 8, the first region R1 of the meat OBJ may be exposed to the first inspection light ILa and ILb to emit first fluorescence OL. The first fluorescence OL may be light emitted after an indicator material in the first region R1 absorbs the first inspection light ILa and ILb. For example, the indicator material may include at least one of porphyrin, collagen, NADH, flavin, and fatty acid.

The first fluorescence OL may pass through the transmission window 120 to be provided in the meat inspection apparatus 10. An optical path of the first fluorescence OL may be adjusted by the optical path control element 20 within the meat inspection apparatus 10 so that the first fluorescence OL is provided to the light detector 200.

The light detector 200 may generate a first emission spectrum signal by detecting and measuring the first fluorescence OL (S120). The first emission spectrum signal may include spectral distribution information of the first fluorescence OL. The light detector 200 may be substantially the same as the light detectors 200, 200a, and 200b described with reference to FIGS. 2, 4, and 5. The spectroscopic first fluorescence OL may be detected by an image sensor included in the light detector 200. The image sensor may include a plurality of pixels. For example, a plurality of pixels may respectively correspond to a plurality of different sub-regions in the first region R1. The first region R1 may be a partial region of meat OBJ to which the first inspection light ILa and ILb is emitted, and the plurality of sub-regions may be regions in the first region R1 corresponding to the plurality of pixels of the image sensor. According to an example embodiment, the plurality of pixels may include a plurality of sub-pixels respectively corresponding to a plurality of wavelength bands. For example, a first sub-pixel may measure light of a first wavelength band, and a second sub-pixel may measure light of a second wavelength band different from the first wavelength band. Accordingly, the image sensor may generate the first emission spectrum signal of the first fluorescence OL emitted from the first region R1. The light detector 200 may provide the first emission spectrum signal to the processor 300.

The processor 300 may generate a first hyperspectral sub-image of the first region based on the first emission spectrum signal (S130). The first hyperspectral sub-image may include spectral distribution information on the first fluorescence OL of each position of the first region R1.

Figure 9:
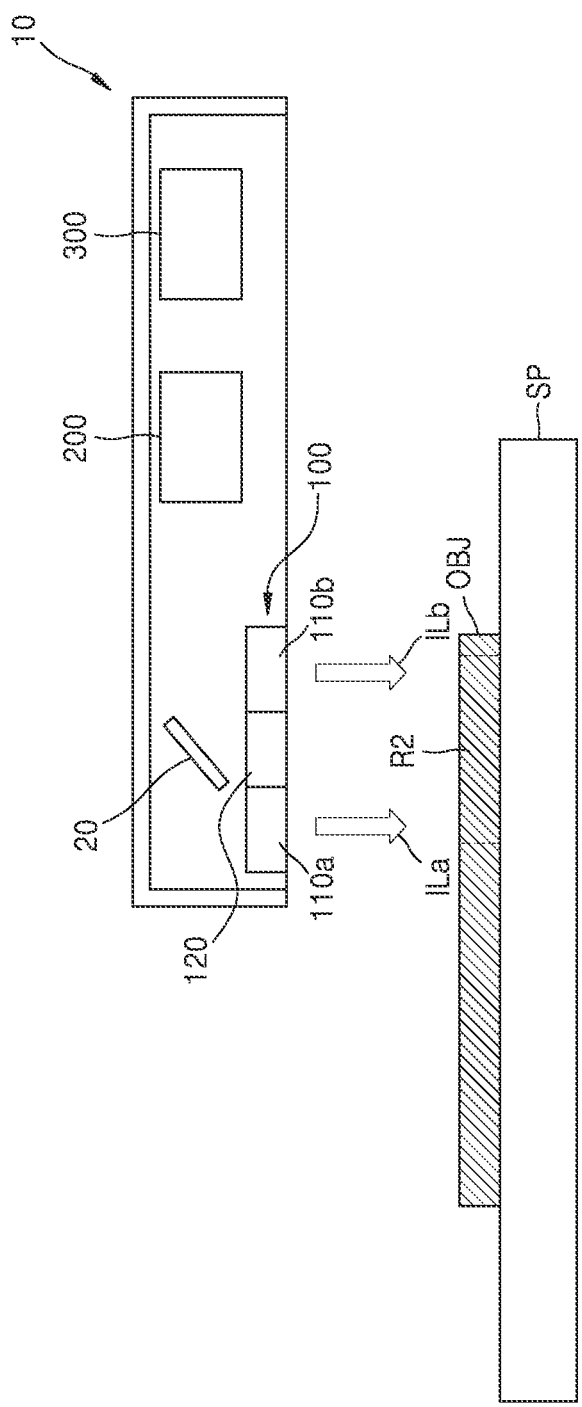

Referring to FIGS. 6 and 9, second inspection light ILa and ILb may be emitted to the second region R2 of the meat OBJ (S140). The meat inspection apparatus 10 may be moved to arrange the light source 100 at a position facing the second region R2. The light source 100 may emit the second inspection light ILa and ILb toward the meat OBJ at the position facing the second region R2. A central wavelength of the second inspection light ILa and ILb may be selected from among approximately 335 nm to approximately 370 nm.

Figure 10:
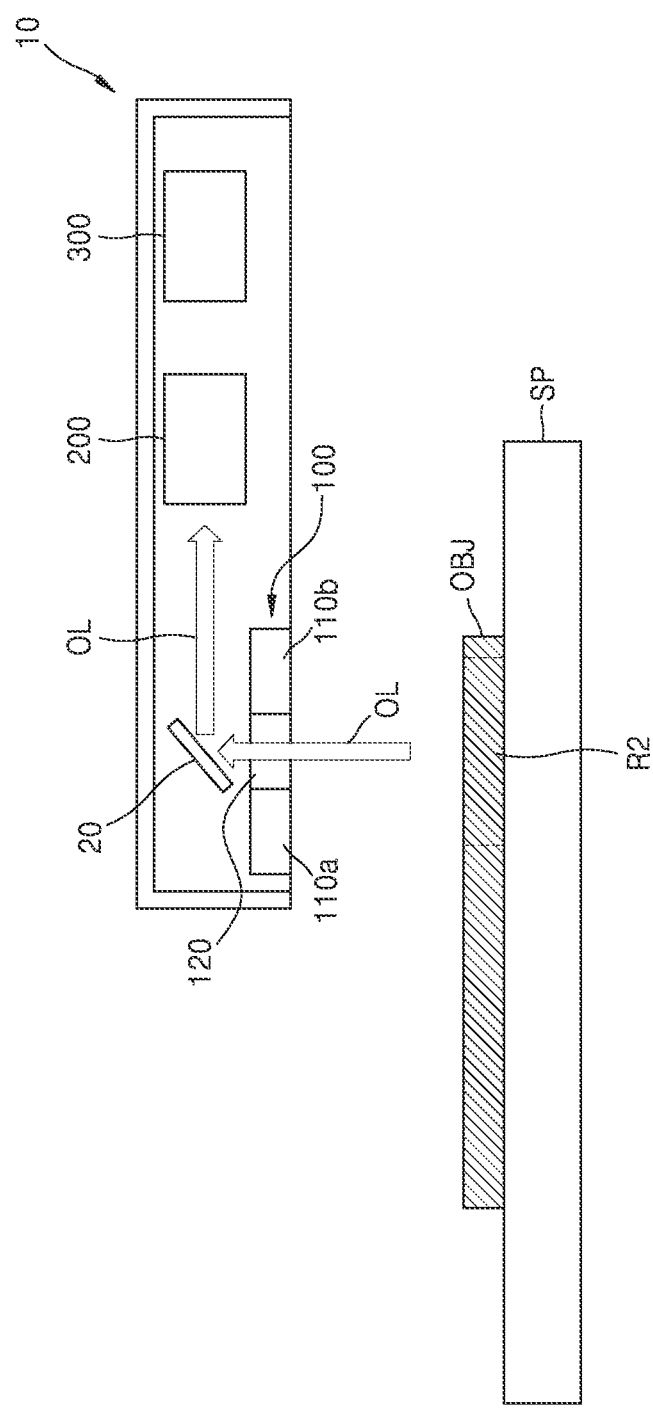

Referring to FIGS. 6 and 10, the second region R2 of the meat OBJ may be exposed to the second inspection lights ILa and ILb to emit second fluorescence OL. The second fluorescence OL may reach the light detector 200 in substantially the same process as the first fluorescence OL.

The light detector 200 may detect and measure the second fluorescence OL to generate a second emission spectrum signal (S150). The second emission spectrum signal may include spectral distribution information of the second fluorescence OL. Generating the second emission spectrum signal may be performed by substantially the same method as generating the first emission spectrum signal. The light detector 200 may provide the second emission spectrum signal to the processor 300.

The processor 300 may generate a second hyperspectral sub-image of the second region based on the second emission spectrum signal (S160). The second hyperspectral sub-image may include spectral distribution information on the second fluorescence OL of each position of the second region R2.

The first region R1 and the second region R2 may partially overlap each other. A region where the first region R1 and the second region R2 overlap may be referred to as an overlap region. The processor 300 may generate all of hyperspectral images by merging the first hyperspectral sub-image with the second hyperspectral sub-image (S170). When merging the first hyperspectral sub-image with the second hyperspectral sub-image, the processor 300 removes a hyperspectral image of an overlap region from any one of the first hyperspectral sub-image and the second hyperspectral sub-image. Accordingly, it is possible to prevent a hyperspectral image of an overlap region from being repeatedly reflected in all of the hyperspectral images.

The processor 300 may measure content distribution of indicator materials in the first region R1 and the second region R2 from all of the hyperspectral images (S180). For example, the processor 300 may measure content distribution of porphyrin based on spectral distribution of a wavelength band of approximately 570 nm to approximately 630 nm. For example, the processor 300 may measure content distribution of collagen based on spectral distribution of a wavelength band of approximately 360 nm to approximately 420 nm. For example, the processor 300 may measure content distribution of NADH based on spectral distribution of a wavelength band of approximately 430 nm to approximately 550 nm. The processor 300 may measure content distribution of flavin based on spectral distribution of a wavelength band of approximately 500 nm to approximately 550 nm. For example, the processor 300 may measure content distribution of fatty acids based on spectral distribution of a wavelength band of approximately 430 nm to approximately 500 nm.

The processor 300 may determine a state of each position of the meat OBJ based on the total content distribution of the indicator materials (S190). The porphyrin, collagen, NADH, and flavin may be indicator materials related to freshness of meat. The processor 300 may determine freshness of each position of the meat OBJ based on content distribution of at least one of porphyrin, collagen, NADH, and flavin or based on a content ratio therebetween. Fatty acid may be an indicator material related to fatness of meat. The processor 300 may determine a degree of fat of each position of the meat OBJ based on content distribution of fatty acid.

According to an example embodiment, a meat inspection method may determine and obtain a state of each position of the meat OBJ by using a hyperspectral image of the meat OBJ.

In another embodiment example, the meat inspection apparatus 10 may include a plurality of meat inspection apparatuses. The plurality of meat inspection apparatuses 10 may determine states of a plurality of regions of the meat OBJ. For example, a pair of the meat inspection apparatuses 10 may be provided to determine states of the first region R1 and the second region R2. The plurality of meat inspection apparatuses 10 may simultaneously perform inspection for a plurality of regions, or may perform inspection at different times.

Figure 11:
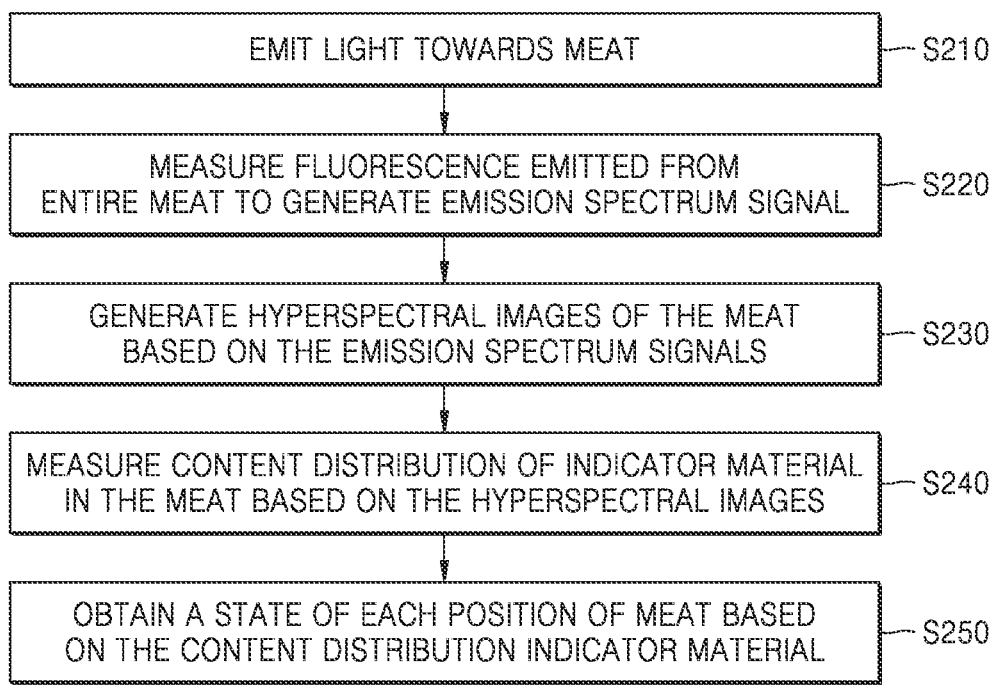
FIG. 11 is a flowchart illustrating a meat inspection method according to an example embodiment.
Figure 12:
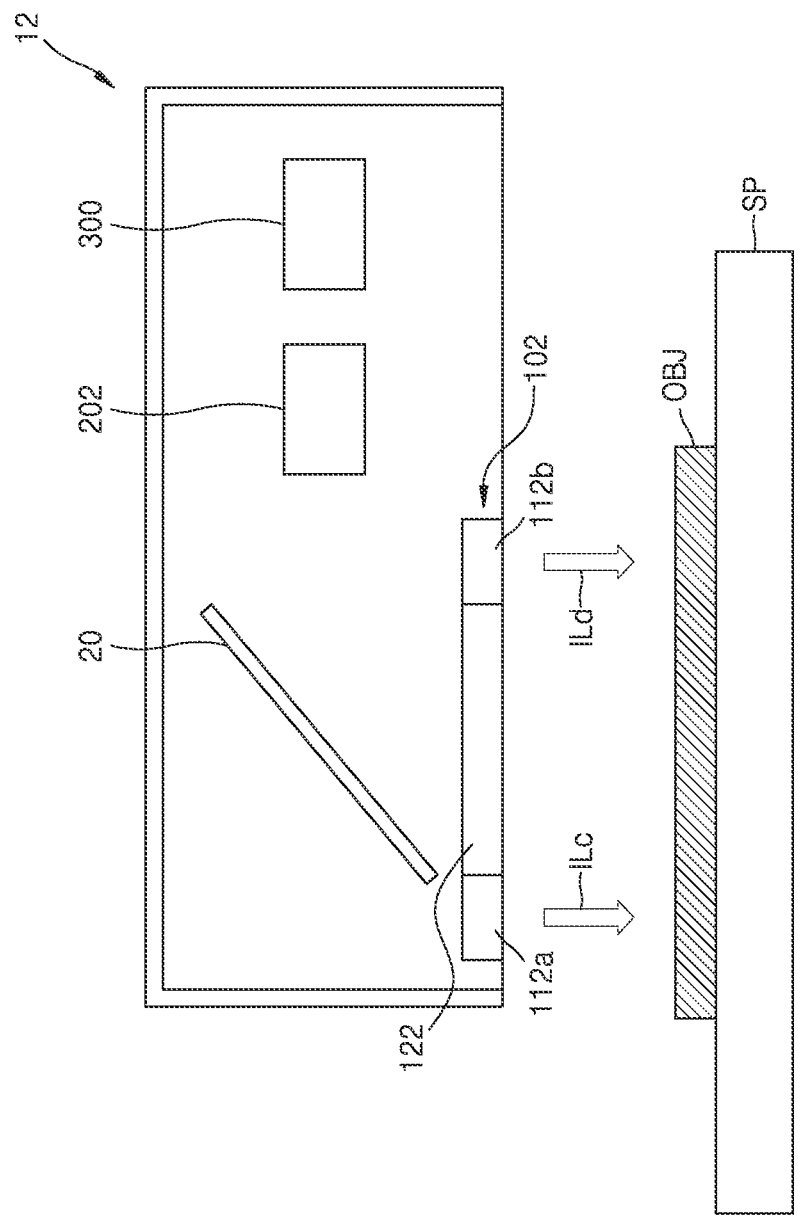
FIGS. 12 and 13 are conceptual views illustrating the meat inspection method of FIG. 11.
Figure 13:
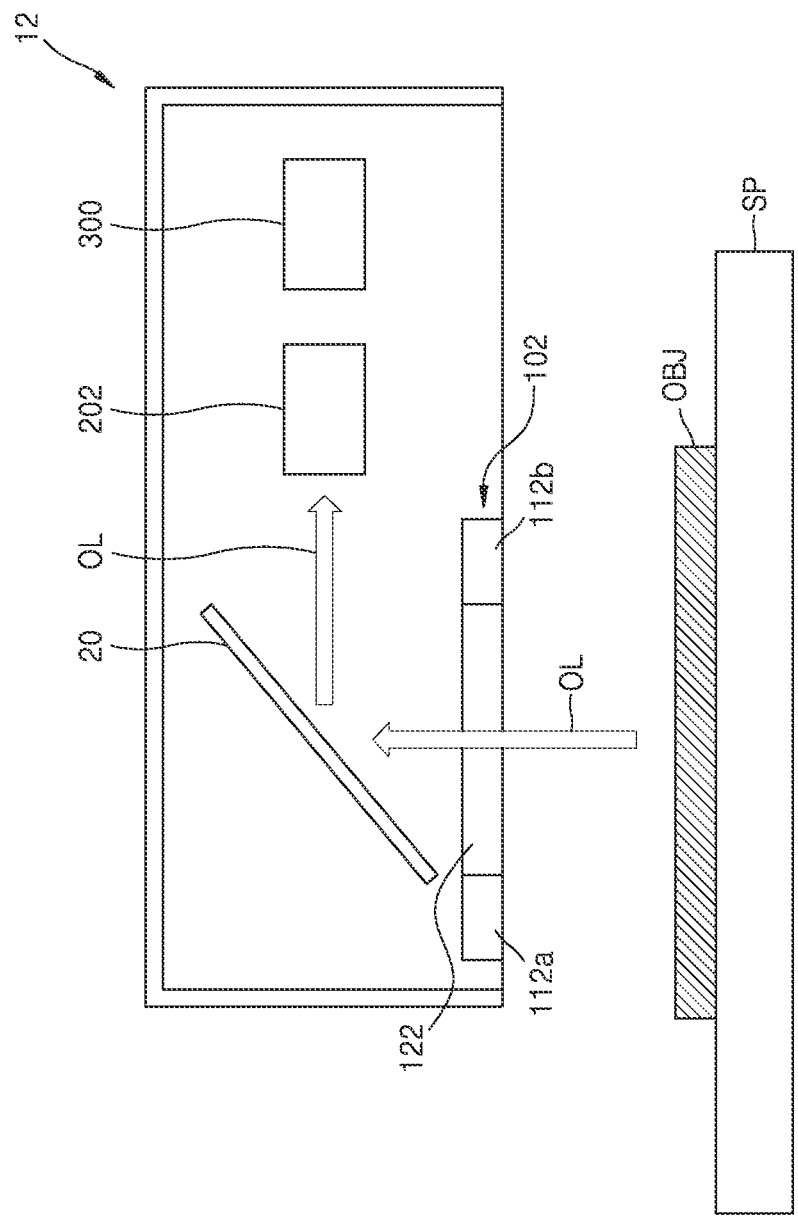

FIG. 11 is a flowchart illustrating an inspection method according to an example embodiment. FIGS. 12 and 13 are conceptual views illustrating the meat inspection method of FIG. 11. The substantially same content as described with reference to FIGS. 2, 4, and 5 and FIGS. 6 to 10 may not be repeated.

Referring to FIGS. 11 and 12, all of the inspection lights ILc and ILd may be emitted onto the meat OBJ (S210). All of the inspection lights ILc and ILd may be emitted from the light source 100. A central wavelength of all of the inspection lights ILc and ILd may be selected from among approximately 335 nm to approximately 370 nm.

Referring to FIGS. 11 and 13, the meat OBJ may be exposed to all of the inspection lights ILc and ILd to emit all fluorescences OL. All of the fluorescences OL may be light emitted after an indicator material in the meat OBJ absorbs all of the inspection lights ILc and ILd. For example, the indicator material may include at least one of porphyrin, collagen, NADH, flavin, and fatty acid.

All of the fluorescences OL may be provided to the light detector 200. A process in which all of the fluorescences OL reaches the light detector 200 may be substantially the same as a process in which the first fluorescence OL described with reference to FIGS. 6 and 8 reaches the light detector 200.

The light detector 200 may receive and measure the total fluorescence OL and generate all emission spectrum signals (S220). The total emission spectrum signal may include spectral information of the total fluorescence OL. The light detector 200 may be substantially the same as the light detectors 200, 200a, 200b described with reference to FIGS. 2, 4, and 5. Spectral fluorescence OL may be detected by an image sensor included in the light detector 200.

The image sensor may include a plurality of pixels. The plurality of pixels may respectively correspond to a plurality of different sub-regions of the meat OBJ. Each of the plurality of pixels may include sub-pixels respectively corresponding to a plurality of wavelengths. Accordingly, the image sensor may generate all of the emission spectrum signals of all fluorescences OL of the meat OBJ.

The light detector 200 may provide all of the emission spectrum signals to the processor 300. The processor 300 may generate all hyperspectral images of the meat OBJ based on all of the emission spectrum signals (S230). All of the hyperspectral images may include spectral distribution information on each position of the meat OBJ for all of the fluorescences OL.

The processor 300 may measure content distribution of indicator material in the meat OBJ based on all of the hyperspectral images (S240). For example, the indicator material may be at least one of porphyrin, collagen, NADH, flavin, and fatty acid. The method of measuring the content distribution of the indicator material by using the processor 300 may be substantially the same as the method of measuring the content distribution of the indicator material described with reference to FIGS. 6 and 10. Unlike that described with reference to FIGS. 6 and 10, all hyperspectral images may be generated based on emitting the inspection lights ILc and ILd once.

The processor 300 may determine a state of each position of the meat OBJ based on all of the content distribution of the indicator material (S250). The processor 300 may determine freshness of each position of the meat OBJ based on the content distribution of at least one of porphyrin, collagen, NADH, and flavin or a content ratio therebetween. The processor 300 may determine a degree of fat of each position of the meat OBJ based on content distribution of fatty acid.

According to an example embodiment, a meat inspection method may determine a state of each position of the meat OBJ by using a hyperspectral image of the meat OBJ.

Figure 14:
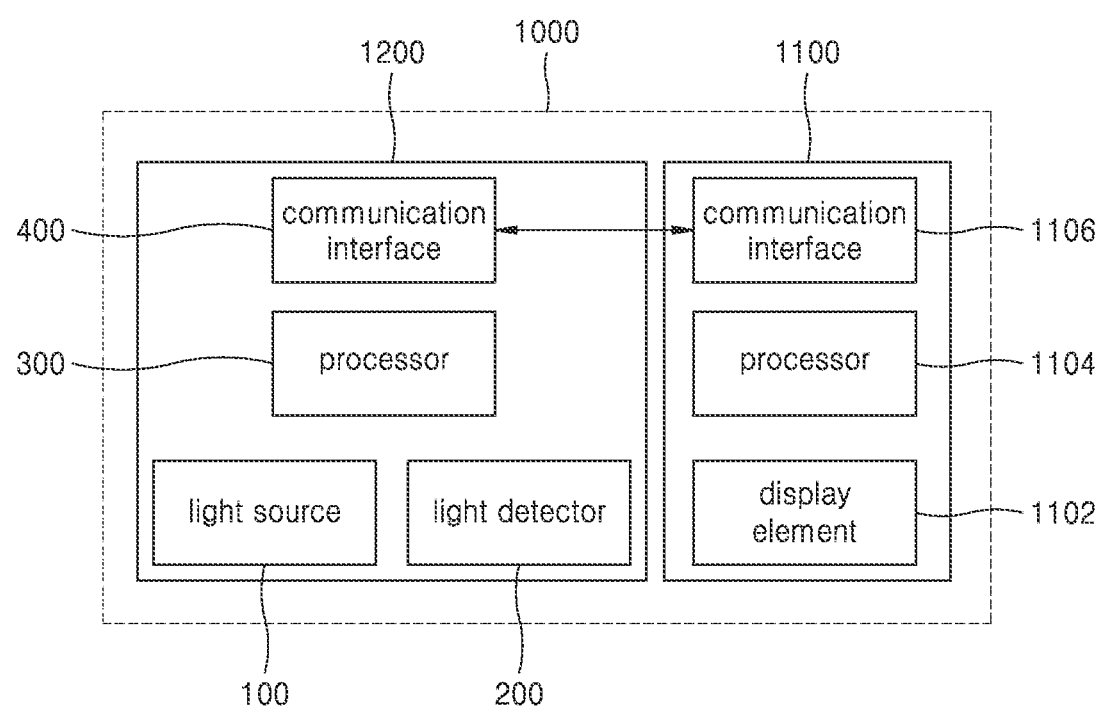
FIG. 14 is a block diagram illustrating a meat inspection system according to an example embodiment.

FIG. 14 is a block diagram illustrating a meat inspection system according to an example embodiment. The substantially same content as in the description made with reference to FIGS. 1 to 5 may not be repeated.

Referring to FIG. 14, a meat inspection system 1000 may include a meat inspection apparatus 1200 and a display device 1100. The meat inspection apparatus 1200 may include a light source 100, a light detector 200, a processor 300, and a communication interface 400. The light source 100, the light detector 200, and the processor 300 are substantially the same as the light source 100, the light detector 200, and the processor 300 described with reference to FIGS. 1 to 5, respectively. The display device 1100 may include a display element 1102, a processor 1104, and a communication interface 1106.

The communication interface 400 of the meat inspection apparatus 1200 may communicate with the communication interface 1106 of the display device 1100 by wire or wirelessly. The communication interface 400 of the meat inspection apparatus 1200 may receive state information of meat from the processor 300. For example, the state information of meat may include freshness of meat and fatness of meat.

The communication interface 400 of the meat inspection apparatus 1200 may provide the state information of meat to the communication interface 1106 of the display device 1100.

The communication interface 1106 of the display device 1100 may provide the state information of meat received from the communication interface 400 of the meat inspection apparatus 1200 to the processor 1104 of the display device 1100. The processor 1104 of the display device 1100 may generate a state output signal based on the state information of meat. The processor 1104 of the display device 1100 may provide the state output signal to the display element 1102.

The display element 1102 may output a video and/or audio including the state information of meat according to the state output signal.

According to the example embodiment, the meat inspection system 1000 may determine and obtain a state of meat and output the state of meat.

Figure 15:
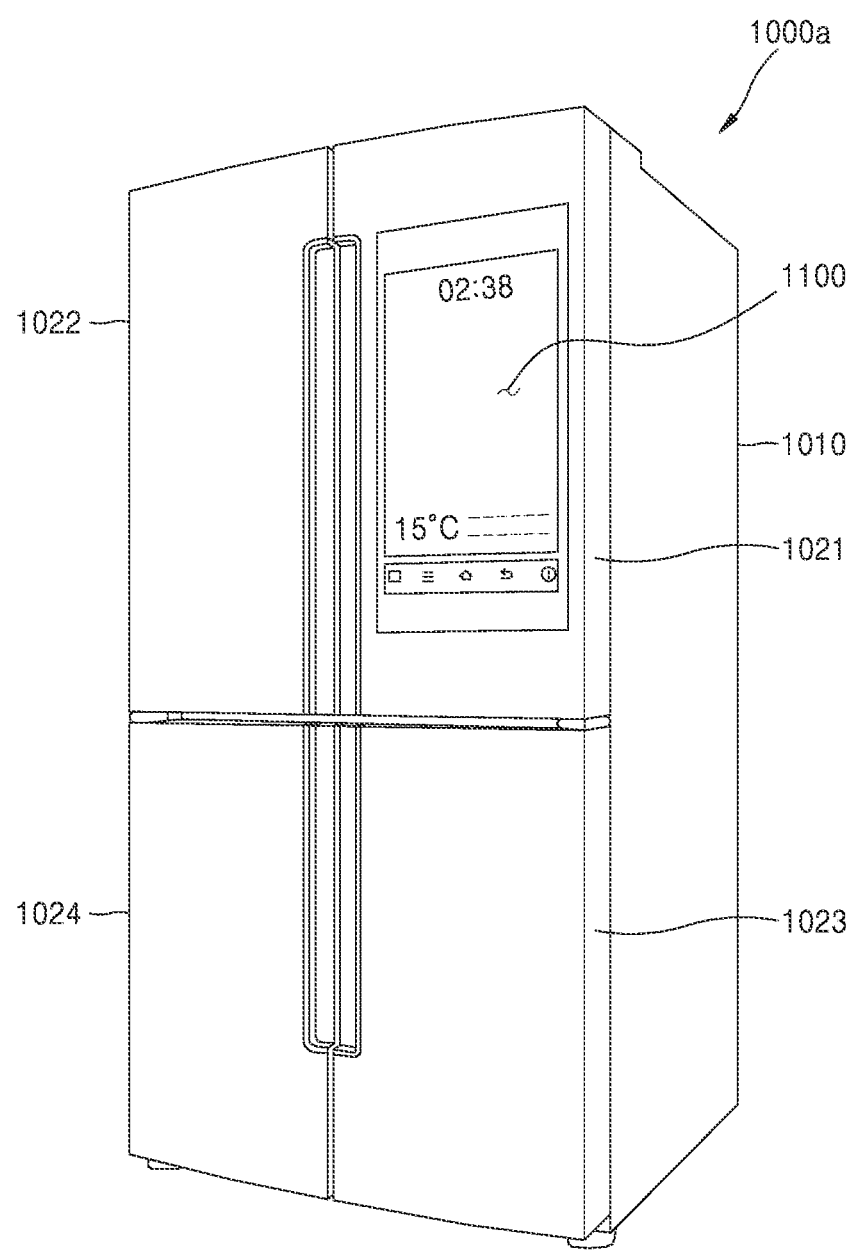
FIG. 15 is a perspective view of a refrigerator according to an example embodiment.
Figure 16:
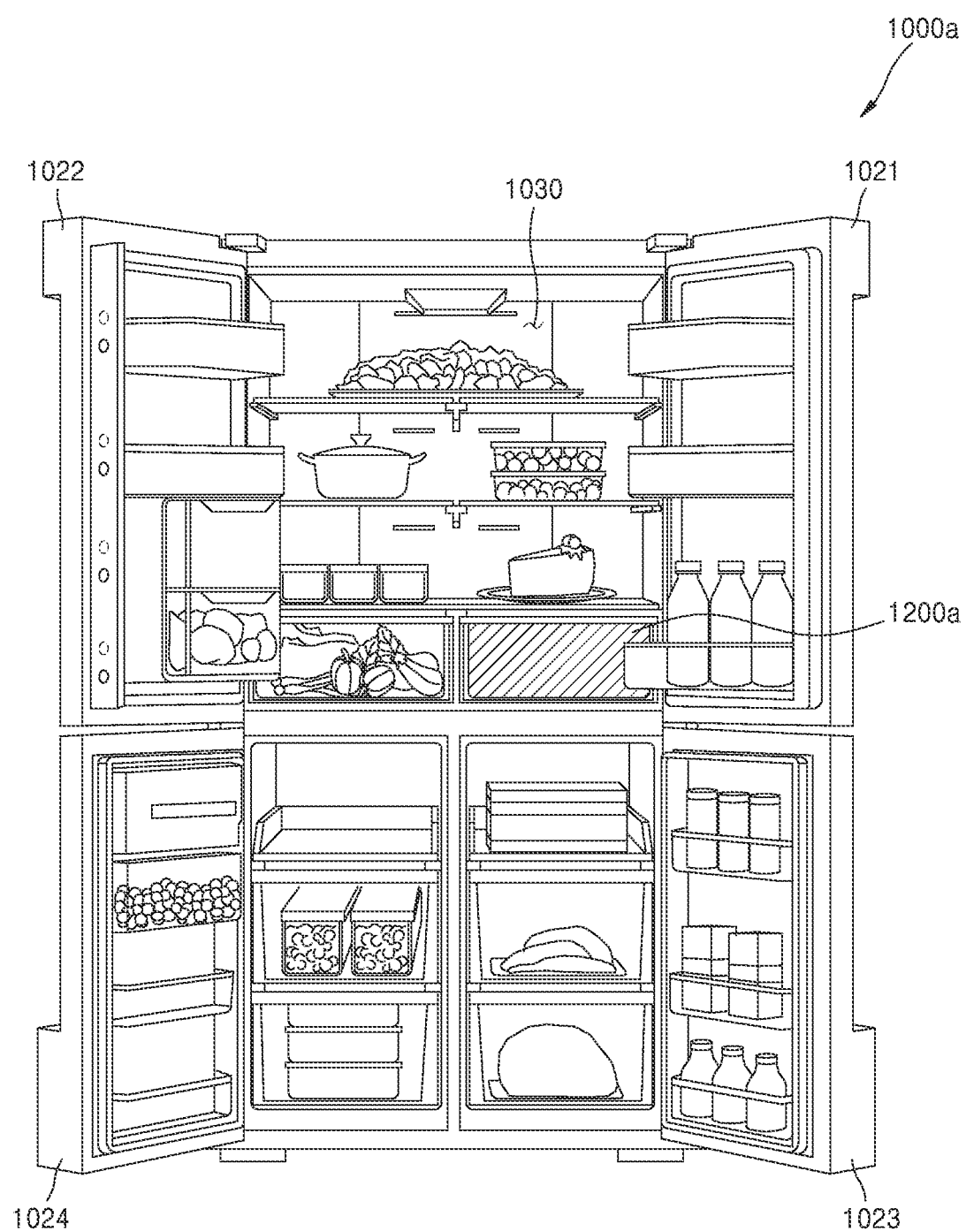
FIG. 16 is a view illustrating a state in which doors of the refrigerator of FIG. 15 are open.

FIG. 15 is a perspective view of a refrigerator according to an example embodiment. FIG. 16 is a view illustrating a state in which doors of the refrigerator of FIG. 15 are open. The substantially same content as in the description made with reference to FIG. 14 may not be repeated.

Referring to FIGS. 15 and 16, a refrigerator 1000a including a main body 1010, doors 1021, 1022, 1023, and 1024, a display device 1100, and a meat inspection apparatus 1200a may be provided. The main body 1010 may include an inner case forming a storage compartment 1030, an outer case forming an appearance of the main body 1010, and a heat insulating material that maintains a temperature difference between the inner case and the outer case. The heat insulating material may prevent cold air inside the storage compartment 1030 from flowing out and external warm air from flowing into the storage compartment.

The main body 1010 may include a cold air supply device that supplies cold air into the storage compartment. The cold air supply device may include a compressor for compressing a refrigerant, a condenser, an expansion valve, an evaporator, and a pipe The storage compartment 1030 may be divided into partitions. The storage compartment may be divided into a freezer compartment and a refrigerator compartment. The freezer compartment may be set to a temperature below zero. The refrigerator compartment may be set to a temperature above zero. For example, water, beverage, food materials, and refrigerated or frozen food may be stored in the storage compartment.

The meat inspection apparatus 1200a may be provided in the storage compartment 1030. The meat inspection apparatus 1200a may be substantially the same as described with reference to FIGS. 1 to 5.

The doors 1021, 1022, 1023, 1024 may include a first door 1021 that opens and closes one side of the refrigerator compartment 1030, a second door 1022 that opens and closes the other side of the refrigerator compartment 1030, a third door 1023 that opens and closes one side of the freezer compartment that opens and closes one side of the freezer compartment, and a fourth door 1024 that opens and closes the other side of the freezer compartment. However, the number of doors is not limited to four.

The display device 1100 may be provided on the front side of the first door 1021. Although the display device 1100 is illustrated as outputting an image, the display device 1100 may include an element that outputs audio as described with reference to FIG. 14. The display device 1100 may provide state information of meat to a user.

According to the example embodiment, the refrigerator 1000a may inspect the state information of meat and provide the state information of meat to the user.

Figure 17:
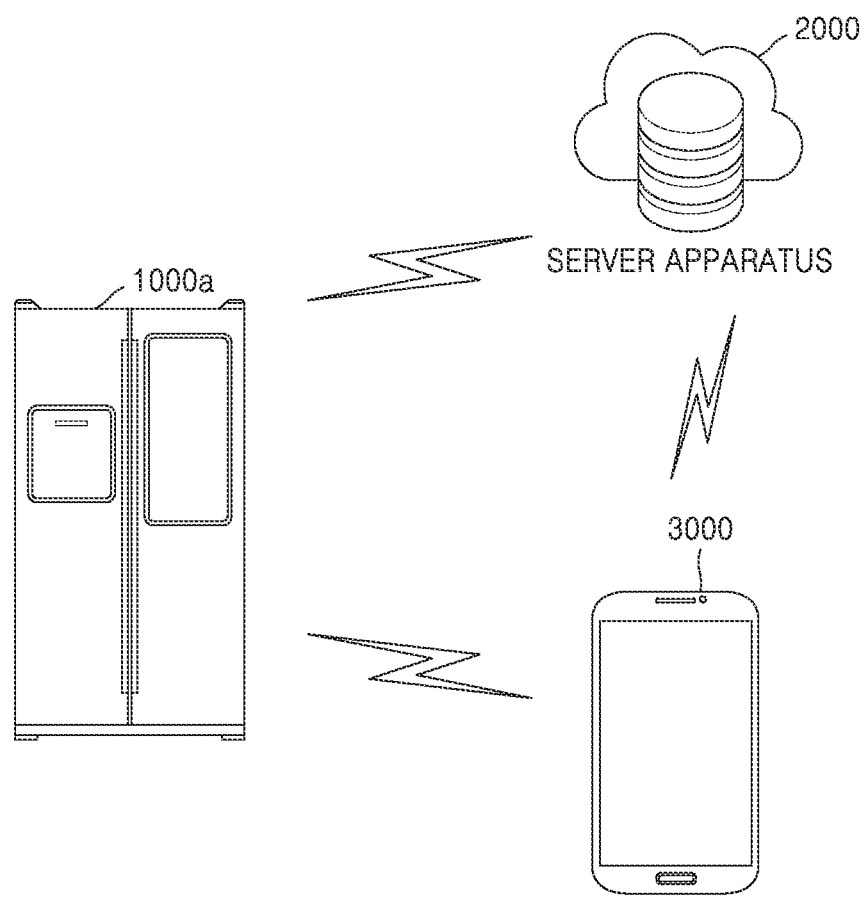
FIG. 17 is a conceptual view of a meat inspection system according to an example embodiment.

FIG. 17 is a conceptual view of the meat inspection system according to the example embodiment. The substantially same content as described with reference to FIGS. 15 and 16 may not be repeated.

Referring to FIG. 17, a meat inspection system including a refrigerator 1000a, a server device 2000, and a mobile terminal 3000 may be provided. The refrigerator 1000a may be substantially the same as the refrigerator 1000a described with reference to FIGS. 15 and 16.

According to an example embodiment, the refrigerator 1000a may include a communication interface for performing communication with an external apparatus. The refrigerator 1000a may communicate with the server device 2000 and/or the mobile terminal 3000 through a communication interface. The communication interface may include a short-range communication unit, a mobile communication unit, and so on. The short-range communication unit (short-range wireless communication interface) may include a Bluetooth communication unit, a Bluetooth low energy (BLE) communication unit, a near field communication interface, a wireless local area network (WLAN) (Wi-Fi) communication unit, a Zigbee communication unit, an infrared data association (IrDA) communication unit, a Wi-Fi direct (WFD) communication unit, an ultra wideband (UWB) communication unit, an Ant+ communication unit, or on the like, and is not limited thereto.

According to an example embodiment, the server device 2000 may include an artificial intelligence (AI) processor. The AI processor may learn an artificial neural network to generate an artificial intelligence model to measure a state of meat. Learning an artificial neural network may indicate generating a mathematical model that may make optimal decisions by connecting neurons which make up the artificial neural network while appropriately changing weighted values based on data.

According to an example embodiment, the server device 2000 may include a communication interface for performing communication with an external apparatus. According to an example embodiment, the server device 2000 may communicate with the refrigerator 1000a or the mobile terminal 3000 through a communication interface. According to an example embodiment, the refrigerator 1000a may access the server device 2000 by transmitting identification information of the refrigerator 1000a or identification information (login information) of a user and by obtaining certification of the identification information of the refrigerator 1000a or the identification information (login information) of the user from the server device 2000.

The mobile terminal 3000 may be a device connected with the same account information as the refrigerator 1000a. The mobile terminal 3000 may also be directly connected to the refrigerator 1000a through a short-range communication link or may also be indirectly connected to the refrigerator 1000 through the server device 2000.

According to an example embodiment, the mobile terminal 3000 may be implemented in various forms. For example, the mobile terminal 3000 may include smart phone, digital camera, laptop computer, tablet PC, e-book terminal, digital broadcasting terminal, personal digital assistant (PDA), portable multimedia player (PMP), navigation, MP3 player, or the like, and is not limited thereto. For example, the mobile terminal 3000 may be a wearable device that may be worn by a user. The wearable device may include at least one of accessory type device (for example, watch, ring, bracelet, anklet, necklace, glasses, or contact lens), head-mounted-device (HMD), fabric or clothing-integrated device (for example, electronic clothing), a body-attached device (for example, skin pad), and bio-implantable device (for example, implantable circuit).

Figure 18:
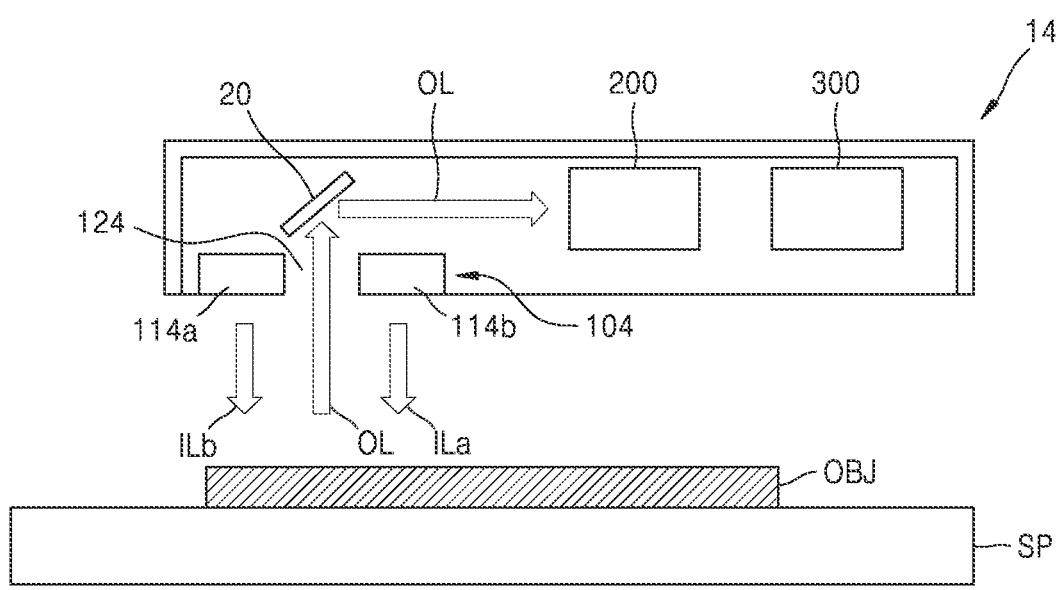
FIG. 18 is a conceptual view of a meat inspection apparatus according to an example embodiment.
Figure 19:
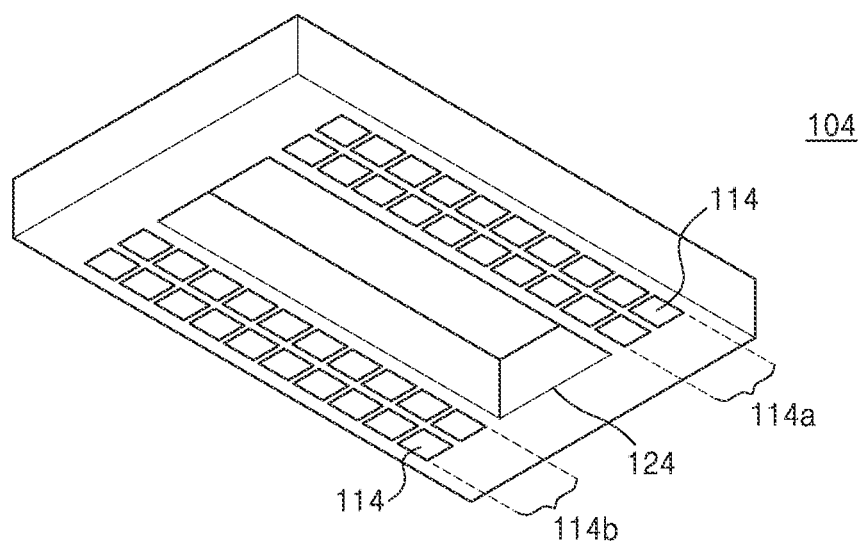
FIG. 19 is an example conceptual view of a light source of FIG. 18.

FIG. 18 is a conceptual view of a meat inspection apparatus according to an example embodiment. FIG. 19 is an example conceptual view of a light source of FIG. 18. The content described with reference to FIGS. 2 to 5 may not be repeated.

Referring to FIGS. 18 and 19, a meat inspection apparatus 14 may be provided. The meat inspection apparatus 14 may include a light source 104, a light detector 200, and a processor 300. The light detector 200 and the processor 300 may be substantially the same as the light detector 200 and the processor 300 described with reference to FIGS. 2 to 5.

As illustrated in FIG. 19, the light source 100 may include a first light source array 114a and a second light source array 114b. Unlike the light source 100 illustrated in FIG. 3, the light source 104 may include an opening 124 instead of the transmission window 120. The first light source array 114a and the second light source array 114b may be spaced apart from each other with the opening 124 therebetween. Each of the first light source array 114a and the second light source array 114b may include a plurality of light sources 114 arranged in one direction. For example, the plurality of light sources 114 may be arranged along the opening 124. Although FIG. 19 illustrates that the plurality of light sources 114 of the first light source array 114a and the second light source array 114b respectively form two rows, embodiments are not limited thereto. The plurality of light sources 114 may include, for example, light emitting diodes (LEDs). The light source 104 may emit inspection light ILa and ILb to meat OBJ. For example, the light source 104 may face the meat OBJ.

The meat OBJ exposed to the inspection light Ila and ILb may emit fluorescence OL. The fluorescence OL may be provided to the inside of the meat inspection apparatus 14 by passing through the opening 124. The fluorescence OL may be provided to the light detector 200. For example, an optical path of the fluorescence OL may be adjusted by an optical path control element 20 such that the fluorescence OL is provided to the light detector 200.

An image sensor 250 in the light detector 200 may generate an emission spectrum signal for the fluorescence OL. The image sensor 250 may provide an emission spectrum signal to the processor 300.

The processor 300 may generate a hyperspectral image of the meat OBJ based on the emission spectrum signal and determine a state of each position of the meat OBJ based on the hyperspectral image of the meat OBJ. For example, a state of the meat OBJ may be freshness of the meat OBJ or fatness of the meat OBJ.

According to an example embodiment, the meat inspection apparatus 14 may determine a state of the meat OBJ by using a hyperspectral image of the meat OBJ.

In another example embodiment, the light source 102 of the meat inspection apparatus 12 described with reference to FIGS. 12 and 13 may also include the opening 124 instead of the transmission window 122.

According to an example embodiment, a meat inspection apparatus may extract a content distribution of an indicator material related to a state of meat by using a hyperspectral image of meat. The meat inspection apparatus may determine the state of meat through the content distribution of an indicator material.

According to an example embodiment, a meat inspection system and a refrigerator may include a meat inspection apparatus for determining and obtaining a state of meat.

According to an example embodiment, a meat inspection method may extract a content distribution of an indicator material related to a state of meat by using a hyperspectral image of meat. The meat inspection method may determine a condition of meat through a content distribution of an indicator material.

However, effects of the disclosure are not limited to the above description.

It should be understood that example embodiments described herein should be considered in a descriptive sense only and not for purposes of limitation. Descriptions of features or aspects within each example embodiment should typically be considered as available for other similar features or aspects in other embodiments. While example embodiments have been described with reference to the figures, it will be understood by those of ordinary skill in the art that various changes in form and details may be made therein without departing from the spirit and scope as defined by the following claims.

What is claimed is:

1. A meat inspection apparatus comprising:
    a light source configured to emit a plurality of inspection lights to a plurality of regions of meat, respectively;
    a light detector configured to generate a plurality of emission spectrum signals based on measuring a plurality of fluorescences emitted from the plurality of regions; and
    a processor configured to:
        receive the plurality of emission spectrum signals from the light detector;
        generate hyperspectral images of the meat based on the plurality of emission spectrum signals; and
        obtain a state of the meat based on the hyperspectral images,
    wherein the processor is further configured to obtain the state of the meat for a plurality of sub-regions in each of the plurality of regions.

2. The meat inspection apparatus of claim 1, wherein the light source is further configured to emit the plurality of inspection lights such that adjacent regions of the plurality of regions partially overlap each other.

3. The meat inspection apparatus of claim 2, wherein the processor is further configured to:
    generate a plurality of hyperspectral sub-images of the plurality of regions;
    merge the plurality of hyperspectral sub-images to generate the hyperspectral images; and
    remove a hyperspectral image corresponding to a region in which the adjacent regions overlap with each other from one of hyperspectral sub-images of the adjacent regions based on the plurality of hyperspectral sub-images being merged.

4. The meat inspection apparatus of claim 1, wherein the light source is further configured to emit the plurality of inspection lights to the plurality of regions at different times.

5. The meat inspection apparatus of claim 4, wherein the light source is disposed at a plurality of positions facing the plurality of regions, and
    wherein the light source is further configured to emit the plurality of inspection lights to the plurality of regions facing the plurality of positions, respectively.

6. The meat inspection apparatus of claim 1, wherein the light source comprises a plurality of sub-light sources configured to emit the plurality of inspection lights to the plurality of regions, respectively, and
    wherein the light detector comprises a plurality of sub-light detectors configured to measure the plurality of fluorescences emitted from the plurality of regions, and
    wherein the processor is further configured to receive the plurality of emission spectrum signals from the plurality of sub-light detectors.

7. The meat inspection apparatus of claim 1, wherein the state of the meat comprises freshness, and
    wherein the processor is further configured to obtain a content of porphyrin in the meat based on the hyperspectral images and obtain the freshness of the meat based on the content of porphyrin.

8. The meat inspection apparatus of claim 1, wherein the state of the meat comprises freshness, and
    wherein the processor is further configured to obtain at least one of a content of collagen in the meat, a content of NADH in the meat, and a content of flavin in the meat based on the hyperspectral images, and obtain the freshness of the meat based on at least one of the content of collagen, the content of NADH, and the content of flavin or based on a ratio therebetween.

9. The meat inspection apparatus of claim 1, wherein the state of the meat comprises a degree of fat, and
    wherein the processor is further configured to obtain a content of fatty acid in the meat based on the hyperspectral images and obtain the degree of fat of the meat based on the content of fatty acid.

10. The meat inspection apparatus of claim 1, wherein the meat comprises a plurality of individual meats, and
    wherein the processor is further configured to distinguish the plurality of individual meats based on hyperspectral images of the plurality of individual meats and obtain a state of each of the plurality of individual meats.

11. The meat inspection apparatus of claim 1, wherein the light source comprises a first light source array comprising a plurality of light sources disposed in a first direction.

12. The meat inspection apparatus of claim 11, wherein the light source further comprises a transmission window, and
    wherein the plurality of fluorescences emitted from the plurality of regions pass through the transmission window to reach the light detector.

13. The meat inspection apparatus of claim 12, wherein the light source further comprises a second light source array spaced apart from the first light source array in a second direction with the transmission window interposed therebetween,
    wherein the second direction crosses the first direction, and
    wherein the second light source array comprises a plurality of light sources disposed in the first direction.

14. The meat inspection apparatus of claim 1, wherein central wavelengths of the plurality of inspection lights range from among 335 nm to 370 nm.

15. A meat inspection system comprising:
    a meat inspection apparatus comprising:
        a light source configured to emit a plurality of inspection lights to a plurality of regions of meat, respectively;
        a light detector configured to generate a plurality of emission spectrum signals based on measuring a plurality of fluorescences emitted from the plurality of regions; and a processor configured to:
   receive the plurality of emission spectrum signals from the light detector;
   generate hyperspectral images of the meat based on the plurality of emission spectrum signals; and
   obtain a state of the meat based on the hyperspectral images,
   wherein the processor is further configured to obtain the state of the meat for a plurality of sub-regions in each of the plurality of regions; and
a display device configured to receive state information of the meat from the meat inspection apparatus and output the state information of the meat.

16. The meat inspection system of claim 15, wherein the display device is connected to the meat inspection apparatus by wire or wirelessly.

17. A refrigerator comprising:
a main body having a plurality of storage spaces;
doors configured to open and close the plurality of storage spaces; and
a meat inspection apparatus provided in at least one of the plurality of storage spaces,
wherein the meat inspection apparatus comprises:
   a light source configured to emit a plurality of inspection lights to a plurality of regions of meat, respectively;
   a light detector configured to generate a plurality of emission spectrum signals based on measuring a plurality of fluorescences emitted from the plurality of regions; and
   a processor configured to:
      receive the plurality of emission spectrum signals from the light detector;
      generate hyperspectral images of the meat based on the plurality of emission spectrum signals; and
      obtain a state of the meat based on the hyperspectral images,
      wherein the processor is further configured to obtain the state of the meat for a plurality of sub-regions in each of the plurality of regions.

18. The refrigerator of claim 17, further comprising:
a display device disposed on one of the doors,
wherein the display device is configured to receive state information of meat from the meat inspection apparatus and output the state information of the meat.

19. The refrigerator of claim 18, further comprising:
a communication interface configured to communicate with an external apparatus,
wherein the communication interface is further configured to transmit the state information of the meat to the external apparatus.

20. A meat inspection method comprising:
emitting a plurality of inspection lights to a plurality of regions of meat;
detecting a plurality of fluorescences emitted from the plurality of regions to generate a plurality of emission spectrum signals;
generating hyperspectral images of the meat based on the plurality of emission spectrum signals; and
obtaining a state of the meat based on the hyperspectral images,
wherein the obtaining of the state of the meat is performed for a plurality of sub-regions of each of the plurality of regions.

21. The meat inspection method of claim 20, wherein the emitting of the plurality of inspection lights further includes emitting the plurality of inspection lights so that adjacent regions of the plurality of regions partially overlap each other.

22. The meat inspection method of claim 21, wherein the generating of the hyperspectral images further comprises:
generating a plurality of hyperspectral sub-images of the plurality of regions;
removing a hyperspectral image of a region in which the adjacent regions overlap each other from one of hyperspectral sub-images of the adjacent regions; and
merging the plurality of hyperspectral sub-images.

23. The meat inspection method of claim 20, wherein the emitting of the plurality of inspection lights to the plurality of regions of the meat is performed at different times.

24. The meat inspection method of claim 20, wherein the emitting of the plurality of inspection lights to the plurality of regions of the meat is performed simultaneously.

25. The meat inspection method of claim 20, wherein the obtaining of the state of the meat further includes obtaining a content of porphyrin in the meat based on the hyperspectral images and obtaining freshness of the meat based on the content of porphyrin.

26. The meat inspection method of claim 20, wherein the obtaining of the state further includes obtaining at least one of a content of collagen in the meat, a content of NADH in the meat, and a content of flavin in the meat based on the hyperspectral images, and obtaining freshness of the meat based on at least one of the content of collagen, the content of NADH, and the content of flavin or based on a ratio therebetween.

27. The meat inspection method of claim 20, wherein the obtaining of the state further includes obtaining a content of fatty acid in the meat based on the hyperspectral images and obtaining a degree of fat of the meat based on the content of the fatty acid.

28. The meat inspection method of claim 20, wherein central wavelengths of the plurality of inspection lights range from among 340 nm to 370 nm.

29. The meat inspection method of claim 20, wherein the meat includes a plurality of individual meats, and
   wherein the obtaining of the state of the meat further includes distinguishing the plurality of individual meats based on hyperspectral images of the plurality of individual meats and obtaining a state of each of the plurality of individual meats.

30. A meat inspection apparatus comprising:
a light source configured to emit a plurality of inspection lights to a plurality of regions of meat, respectively, the light source comprising:
   a first light source array;
   a second light source array that is spaced apart from the first light source array; and
   a transmission window disposed between the first light source array and the second light source array;
a light detector configured to generate a plurality of emission spectrum signals based on measuring a plurality of fluorescences emitted from the plurality of regions; and
a processor configured to:
   receive the plurality of emission spectrum signals from the light detector;
   generate hyperspectral images of the meat based on the plurality of emission spectrum signals; and
   obtain a state of the meat based on the hyperspectral images, wherein the processor is further configured to obtain the state of the meat for a plurality of sub-regions in each of the plurality of regions.

\* \* \* \* \*